United States Patent [19]
Kwan

[11] Patent Number: 5,338,197
[45] Date of Patent: Aug. 16, 1994

[54] DENTAL IMPLANT HAVING CUTTING MEANS

[76] Inventor: Norman H. K. Kwan, 209 Indian Valley Trail, Mississauga, Ontario, Canada, L5G 2K5

[21] Appl. No.: 51,054
[22] Filed: Apr. 21, 1993

[30] Foreign Application Priority Data

Apr. 13, 1993 [CA] Canada .................................. 2093900

[51] Int. Cl.$^5$ ............................................. A61F 5/04
[52] U.S. Cl. ................................................... 433/174
[58] Field of Search ............... 433/169, 173, 174, 175, 433/176

[56] References Cited

U.S. PATENT DOCUMENTS

| | | | |
|---|---|---|---|
| 2,609,604 | 9/1952 | Sprague . | |
| 3,579,831 | 5/1971 | Stevens . | |
| 3,672,058 | 6/1972 | Nikoghossian . | |
| 4,016,651 | 4/1977 | Kawahara et al. . | |
| 4,330,891 | 5/1982 | Branemark et al. . | |
| 4,468,200 | 8/1984 | Munch | 433/174 |
| 4,713,004 | 12/1987 | Linkow et al. | 433/174 |
| 4,854,872 | 8/1989 | Detsch | 433/173 |
| 4,854,873 | 8/1989 | Linden | 433/173 |
| 4,871,313 | 10/1989 | Maillefer | 433/225 |
| 4,932,868 | 6/1990 | Linkow et al. | 433/174 |
| 4,960,381 | 10/1990 | Niznick | 433/174 |
| 5,030,095 | 7/1991 | Niznick | 433/173 |
| 5,061,181 | 10/1991 | Niznick | 433/174 |

FOREIGN PATENT DOCUMENTS 0126624 11/1984 European Pat. Off. ............ 433/174

Primary Examiner—Cary E. O'Connor
Attorney, Agent, or Firm—Vidas, Arrett & Steinkraus

[57] ABSTRACT

An anchor pin for securing an artificial tooth or dental prosthesis to the bone of a patient, having a plurality of cutting flutes disposed about the periphery of a top portion of the pin. The cutting flutes have a substantially right-angled cutting surface perpendicular to the direction of rotation of pin when inserted into the patient's bone, which shaves bone fragments from the bone to allow countersinking of the top portion of the pin within the patient's bone, and which also create and direct such bone fragments to strategic areas of the pin to assist in bone growth around the anchor pin which will prevent removal and loosening of the pin from the bone.

13 Claims, 4 Drawing Sheets

DENTAL IMPLANT HAVING CUTTING MEANS

FIELD OF THE INVENTION

The present invention relates to a dental implant and more particularly to an anchor pin for insertion into a patient's bone, having cutting flutes to assist submerging, anchoring and stablizing the anchor pin in the patient's bone as well as creating and directing bone fragments to strategic areas around the anchor pin to assist in bone growth around the anchor pin which will prevent removal and loosening of the pin from the bone.

BACKGROUND OF THE INVENTION

Screw-type dental implants and in particular externally threaded anchor pins for insertion into dental bone tissue of a patient to support artificial dental appliances, such as an artificial teeth, are well known in the art.

Common examples of such prior art devices are disclosed in U.S. Pat. Nos. 4,932,868 and 4,713,004, 5,061,181, 4,960,381, and 4,468,200.

Since dental anchor pins are generally of a substantially cylindrical shape intended to be completely submerged in bone tissue, with only an extreme upper end surface exposed to abut the prosthetic dental implant, the largest outer diameter of the anchor pin is generally the major thread diameter of the external threads on the pin. This allows a single bore-hole to be made in the patient's bone tissue of a diameter approximately equal to the minor thread diameter of the pin, thereby permitting the anchor pin and the external threads thereon to be fully screwably inserted into the bore-hole (see for example U.S. Pat. No. 4,960,381) in the patient's bone.

Frequently, however, the top portion of the dental pin is needed to both engage a tool to allow screwable insertion into the patient, and to also provide a mating surface for a prosthetic implant, such as an artificial tooth.

Accordingly, the top portion of the pin frequently of necessity needs to be of a diameter larger than the bore-hole diameter, which as mentioned previously, is drilled to the minor thread diameter of the pin. Such a configuration requires countersinking of the bore-hole if the top portion of the pin is to fit into the bone and to be submerged level with the bone tissue of the patient without interference. Countersinking must accordingly be done either by drilling a second larger bore for a portion of the bore-hole, or using a double-sized drill bit, as is disclosed in U.S. Pat. No. 5,061,181, to thereby provide a bore of two diameters.

For example, FIG. 2 of U.S. Pat. No. 5,061,181 (FIG. 1 of the drawings herein) discloses an anchor pin 2, having a top portion 17 of diameter $D_z$ which is larger than the minor thread diameter $D_x$ of threads 46. Such a configuration thereby requires a countersinking operation (i.e. an additional wider bore for a portion of the bore) if the circumferential ridges 39 and top portion 17 of the anchor pin are to be submerged within a drilled bore of diameter $D_x$.

Apart from prolonging the duration of an operation on a patient by requiring the drilling of a second bore, countersinking has an additional drawback in that countersinking removes additional dental bone from the mouth of the patient. This ground bone, because of its cortical nature, is extremely useful in anchoring the dental implant, as it can greatly speed and assist in bone growth around the implant. Accordingly, it is very desirable that the ground bone and bone chips be retained in the bore if at all possible to assist in autogenous rapid re-growth of bone around the prosthetic anchor pin to thereby assist in anchoring the pin within the patient's bone tissue.

Recently-developed anchor pins, such as the anchor pin 10 disclosed in both U.S. Pat. No. 4,713,004 and 4,932,860 (see FIG. 2 thereof and FIG. 2A and 2B of the drawings herein) make use of this concept. For example, U.S. Pat. No. 4,713,004 discloses channels 18 formed in anchor pin 10 which extend through the threads 13, 13' on the body of the anchor pin 10. Threads 13 along one side edge of the channel 18 are disposed at a right angle to the circumferential direction of rotation A of the pin 10 while the threads 13' (see FIG. 2 of the drawings herein) on the other side edge of the channel 18 are at an oblique angle to the circumferential direction of rotation A of the pin 10. This allows the right-angled edge of threads 13 to shave off bone chips during threading of the pin into the bone, and to direct the pieces of bone into the channel 18 and vent 16, so that pieces of bone are directed to the base portion of the bore-hole and the pin to assist in bone growth in this area, thereby improving the anchoring of the pin 10 to the patient's bone.

Notably, however, the diameter $D_z$ of the top portion of the pin 10 is typically greater than the minor diameter of the threads $D_x$, particularly where a sufficient mating surface area is required to accommodate a hex nut and at the same time provide a sufficient mating surface for the artificial tooth (see for example the prior art anchor pin 10 shown in FIG. 2A and 2B herein and U.S. Pat. No. 4,713,004). Thus countersinking is necessary and should be done if the top portion of the pin 10 is to be fully submerged.

If countersinking is not carried out, although the self-tapping threads 13 remove some of the bone material when the pin is threadably inserted into the patient, the top portion 16 of the anchor pin 10 because of its larger diameter DZ will be forcibly compressed against bone tissue surrounding the smaller diameter bore-hole of diameter Dx, upon full insertion of the pin 10. This has been found to be extremely undesirable, as it tends to strip the threaded bone tissue, and in addition because of the larger diameter it tends to be compressed against the bone thereby impeding circulation in the bone tissue surrounding the top portion 16 of the implant (pin), resulting poor bone structure surrounding the implant, and thus a much weaker dental implant. As well, valuable bone chips for the area of the bore displaced by the top portion 16 of the pin 10 are not utilized nor displaced elsewhere to other locations proximate the pin 10 to assist in reestablishing bone growth around the anchor pin 10.

Accordingly, despite the prior art, a real and substantial need exists for a dental anchor pin which has a top portion of a diameter greater than the minor thread diameter of the pin, but does not require a separate countersinking operation. A real need further exists for an anchor pin that is able to self-countersink and utilize and relocate bone chips from the self-countersinking operation to assist in autogenous regeneration of bone at same or other locations around the prosthetic anchor pin.

SUMMARY OF THE INVENTION

Accordingly, in order to meet the above-expressed needs, the present invention provides for a novel anchor pin having a top portion of a diameter greater than the minor thread diameter thereon, which is able to self countersink and also make use of bone chips created during the countersinking to assist in bone growth around the anchor pin which will prevent removal and loosening of the pin from the bone.

In a broad aspect, the anchor pin of the present invention comprises a substantially cylindrical body portion of diameter Dx having external raised threads thereon, adapted to be screwably inserted into a bone of a patient in the vicinity of the occlusal plane (mouth) of a patient. The anchor pin may be of the self-tapping type, or adapted to be rotatably inserted into a pre-drilled (tapped) bore of diameter Dx in the patients.

The anchor pin of the present invention possesses a top portion abutting its body portion of maximum diameter Dz, where diameter Dz is greater than diameter Dx. The top portion is adapted to support an artificial tooth structure or dental prosthesis.

Importantly, and essential to the invention described herein, the top portion of the anchor pin possesses a plurality of circumferentially-disposed cutting means (members) located about a periphery thereof, each of such cutting members adapted, when the implant is rotatably inserted to a bore-hole in the patient's mouth, to:

(i) allow countersinking of the top portion of the pin within the patient's bone; and (ii) to shave off fragments of bone and retain such fragments in close proximity and in abutting relation with the implant to assist in bone growth around the implant.

These cutting means not only provide a "grip" at the final seating of the implant to thereby prevent further continued rotation of the implant, but also displace bone chips, principally by cutting away threads which would otherwise be forcibly compressed upon the insertion of the larger diameter top portion of the pin.

In a preferred embodiment, the cutting means or members consists of a plurality of cutting flutes which are circumferentially disposed about the periphery of the top portion of the anchor pin. Each cuttings flute has a radially outwardly-extending cutting surface at substantially a right-angle to the direction of rotation of the implant when rotatably inserted into the patient's bone.

In a further preferred embodiment, a lowermost portion of the top portion of the anchor pin is of a downwardly extending, radially converging, substantially frusto-conical shape, and each of the cutting flutes comprises indented notches circumferentially disposed about the periphery of the frusto-conical surface. Advantageously, the indented notches, after they have served their function of shaving off fragments of bone during the countersinking operation, serve as a cavity to retain bone fragments therein. These bone fragments then speed and assist bone growth into the indented notches. Such regrown bone then serves to prevent the anchor pin from rotation and thus assists in anchoring the anchor pin within the patient's bone and prevent removal of the pin.

In an important further aspect of this invention, anchoring of the anchor pin in the bone of a patient is further assisted and increased by a co-operative relationship between the cutting flutes and one or more grooves within the body portion of the anchor pin.

Accordingly, in this further aspect of the invention, the cutting means is further adapted during rotatable insertion of the anchor pin in the patient's bone to shave off bone fragments during the countersinking operation and further direct the base fragments into the groove(s) on the anchor pin, which each serve as a cavity to collect such bone fragments. These bone fragments likewise ensure and assist bone growth into the grooves, thereby preventing unwanted rotation and/or removal of the anchor pin from the patient's mouth.

The groove(s) may be a longitudinal channel, or a circumferential groove. In a preferred embodiment, however, the groove consists of a single circumferential groove on the body portion of the pin immediately beneath the top portion and extending radially inwardly to a distance less than diameter Dx. The indented notches on the downwardly-extending frusto-conical surface extend radially inwardly so as to be in communication with the circumferential groove. Accordingly, the indented notches are able to direct bone fragments into the groove. These bone fragments operate to encourage bone growth within the circumferential groove, thereby preventing removal of the pin and thus assisting in anchoring it in the bone. Where a longitudinal instead of a circumferential grooves is utilized, the co-operation between the indented notches and the longitudinal groove is the same as for the circumferential groove, except that for longitudinal groove, when bone solidifies and grows therein, the longitudinal does not directly operate to prevent removal of the pin as in the case of the circumferential groove, but rather operates to prevent rotation of the anchor pin, thereby preventing unwanted screwable removable of the anchor pin.

BRIEF DESCRIPTION OF THE DRAWING

Further objects and advantages will appear from the following detailed description of the invention, taken together with the accompanying drawings in which.

DETAILED DESCRIPTION OF THE DRAWINGS

Figure 1:
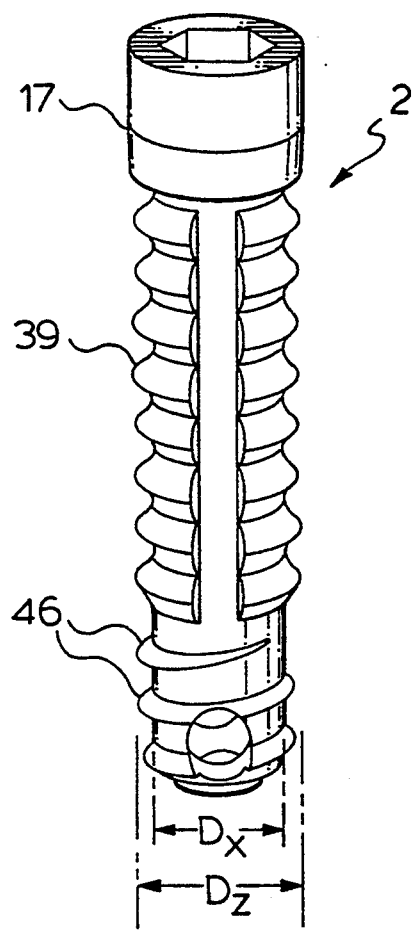
FIG. 1 is a perspective view of one type of anchor pin of the prior art.

FIGS. 3–7 show the oral implant of the present invention, comprising a dental anchor pin 50 adapted to support and be fixably attached to an artificial tooth structure or dental prosthesis such as a bridge (not shown).

The anchor pin 50 of the present invention generally comprises a substantially cylindrical body portion 52 of approximate diameter Dx, having raised external helical threads 53 of diameter Dy thereon extending over a substantial portion thereof, to allow threadable rotatable insertion of the pin 50 into a bore-hole of diameter Dx in the patient's mouth.

The anchor pin 50 is adapted to be rotatably (screwably) inserted into human bone tissue in the occlusal plane (mouth) of a patient, such as the mandibular bone (jawbone) of a patient, to thereby anchor an artificial tooth or dental prosthesis thereto.

Since anchor pins 50 are generally threadably inserted into a pre-drilled bore-hole in the patient's bone of uniform diameter Dx, the body portion 52 and the helical threads 53 thereon need only be cylindrical, as opposed to tapered which they both would otherwise have to be if the pin 50 was to be self-tapping and no pre-drilled bore-hole was to be provided. A frusto-conical distal end 51 is generally provided, to assist in locating the anchor pin 50 in the bore-hole in the patient's mouth.

Figure 4:
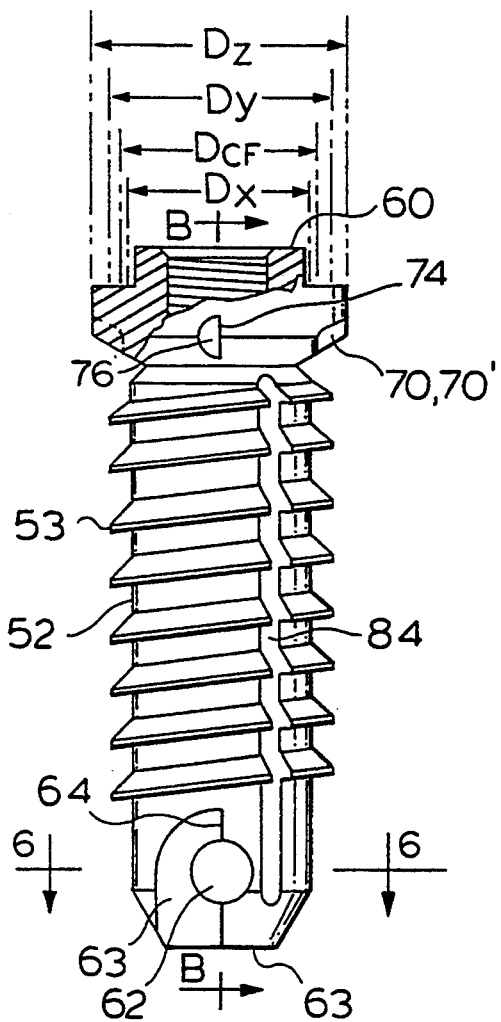
FIG. 4 is a side elevation view in partial cross-section of the oral (dental) implant shown in FIG. 3.

The anchor pin 50 of the present invention possesses a top portion 56 above the body portion 52 thereof, of maximum diameter Dz (see FIG. 4). Located axially on uppermost portion of the top portion 56 of the anchor pin 50 is a hexagonal nut 58. Hex nut 58 allows a griping tool to grip the anchor pin 50 for rotatable insertion of the anchor pin 50 into the patient.

The hex nut 58 abuts a flat surface 59 concentric about the longitudinal axis of the pin 50. The flat surface 59 provides a mating surface which the artificial tooth may abut to thereby provide stability and act as a conduit for transferring forces that are applied to artificial tooth through to the lower body portion 52 of the anchor pin.

Figure 7:
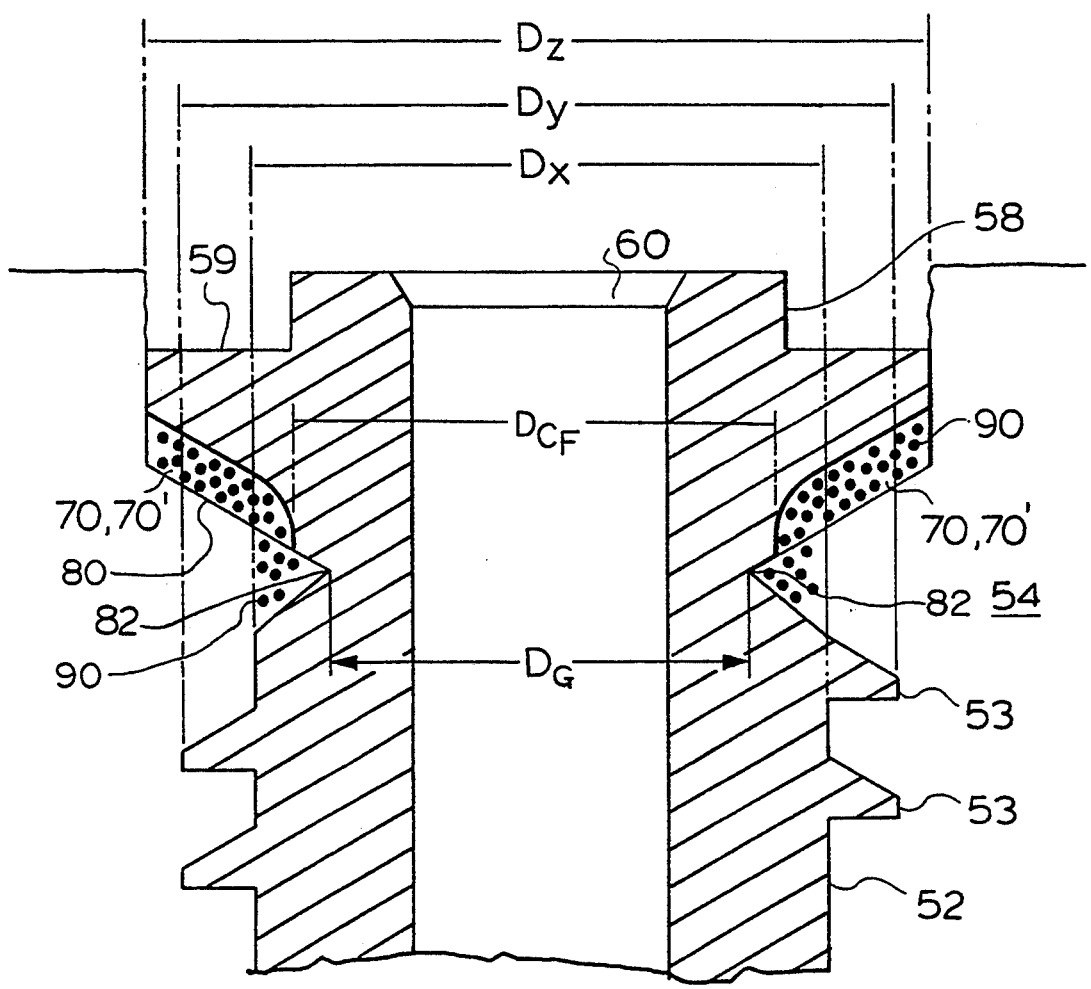
FIG. 7 is a partial cross-section of the oral (dental) implant shown in FIG. 3, taken along plane 7—7 after the implant is installed in the bone of a patient, showing the bone chips relocated to the circumferential groove in the anchor pin.

The pin 50 possesses a longitudinally disposed internally threaded passageway 60 to which an externally-threaded male member (not shown) of the artificial tooth or dental prosthesis is threadably inserted after the anchor pin 50 been submerged in the patient's bone tissue 54 (see FIG. 7). The anchor pin 50 further possesses within its body portion 52 a lateral through-hole 62 perpendicularly disposed to the longitudinal axis of the anchor pin 50. Through-hole 62 is preferably located at the distal end 63 of the anchor pin (i.e. the end opposite the top portion 56). The through-hole 62 provides an aperture through which bone chips may enter and thereby promote bone growth within the through-hole 62. Bone growth within the through-hole 62 assists in preventing rotation of the anchor pin 50, and thereby prevents undesirable loosening or extraction of the pin. Advantageously, because of the desirability of having bone fragments enter the through-hole 62 to thereby promote growth of bone therein, there is further provided in the anchor pin 10 of the present invention cutting means integral with the through-hole 62 to cooperate with the through-hole 62 and shave off fragments of bone when the implant 50 is rotatably inserted in the bone, and efficiently direct such bone fragments directly into the through-hole 62.

Figure 2B:
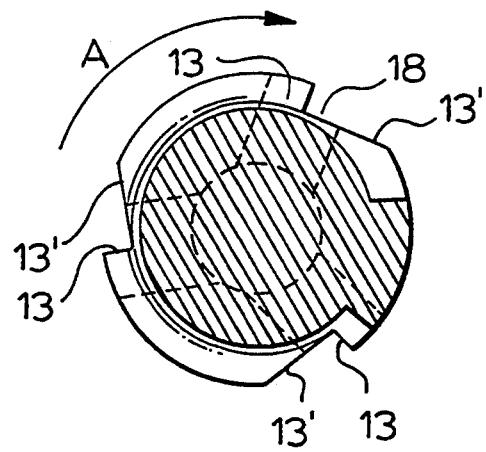
FIG. 2B is a sectional view taken along plane 2B—2B of the prior art anchor pin of FIG. 2A.
Figure 2A:
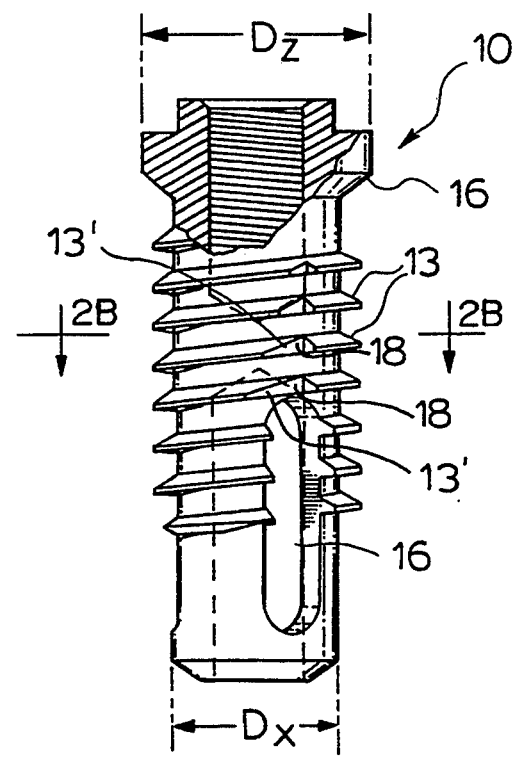
FIG. 2A is a side elevation view in partial cross-section of another type of anchor pin of the prior art.
Figure 5:
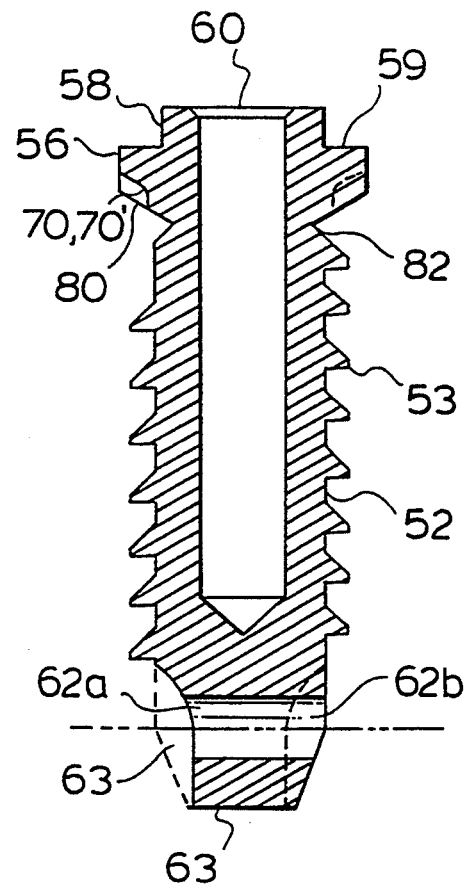
FIG. 5 is a cross-sectional view of the oral (dental) implant shown in FIG. 4, taken along plane 5—5.
Figure 6:
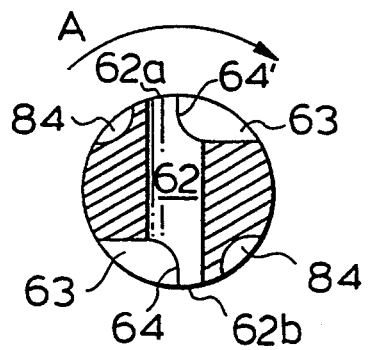
FIG. 6 is a cross-sectional view of the oral (dental) implant shown in FIG. 4, taken along plane 6—6.

While the prior art provided channels 18, and more particularly provided right-angled portions of thread 13' near (but not at) the vent 16 (see FIG. 2A) for the purpose of cutting and directing bone chips left after the cutting action of the right-angled threads 13' into the vent 16 (see FIG. 2A), the present invention on the other hand provides for right-angled cutting surfaces 64 directly at and integral with the through-hole 62 and bisecting the through-hole 62 along a longitudinal diameter thereof as shown in FIGS. 4-6. The right-angled cutting surfaces 64, 64' of the present invention are in the preferred embodiment provided by making a notch 65 (preferably machined) in the pin 50 at the location of the through-hole 62 (see FIGS. 3-6).

Accordingly, by having cutting surfaces 64, 64' disposed at respective opposite ends 62a, 62b of the through-hole and perpendicularly disposed to the circumferential direction of rotation A of the anchor pin 50, such cutting surfaces 64, 64' will both cut and direct all or a substantial portion of the bone fragments into the through-hole 62.

Most importantly, however, one of the most significant improvements of the anchor pin 50 of the present invention over the prior art resides in the provision of a plurality of circumferentially-disposed cutting means 70 located about the periphery 72 of the top portion 56 of the pin 50, to allow both (i) countersinking of the top portion 56 within the smaller diameter bore-hole in the patient's bone of diameter Dx, and (ii) the shaving off of fragments of bone during countersinking, and the retention and/or direction of such bone fragments to strategic areas around the anchor pin 50 to thereby assist bone re-growth around the anchor pin and thus securement of the pin in the bone.

Accordingly, in the preferred embodiment of the invention shown in FIGS. 3, 4, 5 and 7, the cutting means 70 comprises a plurality of cutting flutes in the form of indented notches 70', each indented notch 70' having a radially outwardly-extending cutting surface 74 at substantially a right angle to the circumferential direction of rotation A of the anchor pin 50. When the pin 50 is inserted into the patient's bone, perpendicular cutting surface 74 operates as a leading edge, while remaining indented portion 76 of the indented notch 70' operates as a trailing edge.

Figure 3:
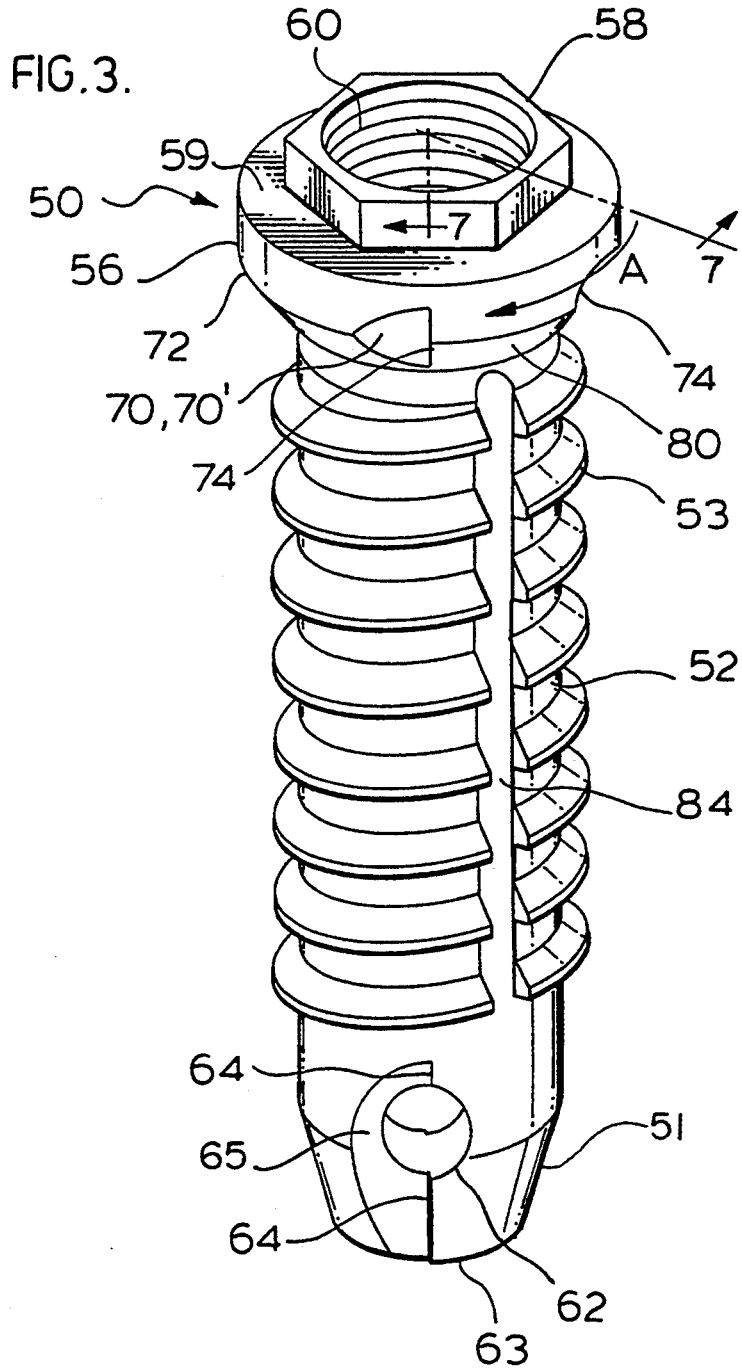
FIG. 3 is a perspective view of the oral implant (dental anchor pin) of the present invention, showing the countersinking cutting means.

In a further refinement of the present invention, the lowermost portion of the top portion 56 is uniformly downwardly extending and radially converging, thereby forming a substantially frusto-conical surface 80, as shown in FIG. 3. Each of the indented notches 70' are circumferentially disposed about the periphery of the frusto-conical surface 80. In such manner the indented notches 70' are ideally positioned to provide countersinking of the larger-diameter top portion 56 within the smaller diameter bore-Role Dx.

Advantageously, in a still further embodiment, again shown in FIGS. 3, 4, 5 and 7, groove means are provided which act as a cavity and are located so as to be able to receive bone fragments created by operation of the cutting surface 74 when the pin 50 is inserted. Such groove means provide a receptacle or reservoir for bone fragments. Growth of bone within such groove means prevents the anchor pin 50 from being removed from the patient.

More particularly, in a preferred embodiment, these groove means comprises a substantially circumferential groove 82 situate immediately beneath but adjacent the top portion 56 of the pin, as shown explicitly in FIG. 3 and 7. Such groove 82 extends radially inward and is of a diameter DG, DG being less than the diameter Dx of the bore-hole and the body portion 52. Cutting flutes 70' (indented notches) extend radially inwardly from the periphery of the top portion 56, so as to direct bone fragments 90 into the circumferential groove 82, as clearly shown in FIG. 7.

In an alternative, or additional configuration, the groove means comprises a longitudinal channel 84 within the body portion 52 of the pin 50, which extends downwardly from a position immediately beneath and adjacent the top portion 56, (see FIGS. 3 and 4). Likewise, in this embodiment, the indented notches 70' extend radially inwardly to a diameter less than Dx so as to be in communication with the longitudinal channel 84, as shown in FIG. 3, to allow the cutting flutes (indented notches 70') to be able to direct bone fragments into, or receive bone fragments from, the longitudinal channel 84.

FIGS. 3 and 4 show an embodiment of the invention incorporating both a circumferential groove 82 and a longitudinal channel 84. When bone fragments solidify and bone growth is re-established in such areas, the groove 82 and the longitudinal channel 84 both serve to prevent the anchor pin from rotation and/or removal from the bore-hole in the patient's bone.

Although the disclosure describes and illustrates preferred embodiments of the invention, it is to be understood that the invention is not limited to these particular embodiments. Many variations and modifications will now occur to those skilled in the art. For definition of the invention, reference is to be made to the appended claims.

I claim:

1. An oral implant for supporting an artificial tooth structure or dental prosthesis, comprising:
   a substantially cylindrical body portion of diameter Dx having raised threads over a lower portion thereof and adapted to be rotatably inserted into a bone of a patient in the vicinity of the occlusal plane;
   a top portion of maximum diameter Dz abutting said body portion where diameter Dz is greater than diameter Dx, adapted to support said artificial tooth structure or dental prosthesis;
   said top portion having circumferentially-disposed cutting means located about a periphery thereof; and
   said cutting means adapted, when the said implant is rotatably inserted in the bone:
      (i) to allow countersinking of the top portion within the patient's bone; and
      (ii) to shave off fragments of bone and retain such bone fragments in close proximity with said implant to assist bone growth around said implant and prevent removal of the implant from the bone.

2. The oral implant as claimed in claim 1 wherein
   said cutting means comprising a plurality of cutting flutes circumferentially disposed about a periphery of said top portion; and
   each cutting flute having a radially outwardly-extending cutting surface at substantially a right angle to the circumferential direction of rotation of the implant when rotatably inserted into the patient's bone.

3. The oral implant as claimed in claim 2 wherein
   a lowermost portion of said top-portion being uniformly downwardly extending and radially converging thereby forming a substantially frusto-conical surface; and
   each of said cutting flutes comprising indented notches, said notches disposed about the periphery of said frusto-conical surface.

4. The oral implant as claimed in claim 3, said raised threads on said lower portion of said cylindrical body portion having diameter D, wherein diameter Dz is greater than diameter Dy.

5. The oral implant as claimed in claim 4 wherein
   said body portion having groove means to receive bone and allow bone to grow therein; and
   said cutting flutes extending radially inwardly from the periphery of said top portion so as to permit the indented notches of said cutting flutes to direct bone fragments into said groove means.

6. The oral implant as claimed in claim 5 wherein
   said groove means comprising a substantially circumferential groove immediately beneath but adjacent said top portion of said implant, extending radially inwardly to a distance less than diameter $D_x$; and
   said indented notches extending radially inwardly so as to be in communication with said circumferential groove and be able to direct bone fragments into said circumferential groove upon rotatable insertion of the implant in the patient's bone.

7. The oral implant as claimed in claim 5 wherein
   said groove means comprising a longitudinal channel within said body portion extending downwardly from a position immediately beneath and adjacent said top portion; and
   said indented notches extending radially inwardly so as to be in communication with said longitudinal channel and be able to direct bone fragments into said longitudinal channel upon rotatable insertion of the implant in the patient's bone.

8. The oral implant as claimed in claim 3 wherein
   said body portion having groove means to receive bone and allow bone to grow therein; and
   said cutting flutes extending radially inwardly from the periphery of said top portion so as to permit the indented notches of said cutting flutes to direct bone fragments into said groove means.

9. The oral implant as claimed in claim 8 wherein
   said groove means comprising a substantially circumferential groove immediately beneath but adjacent said top portion of said implant, extending radially inwardly to a distance less than diameter $D_x$; and
   said indented notches extending radially inwardly so as to be in communication with said circumferential groove and be able to direct bone fragments into said circumferential groove upon rotatable insertion of the implant in the patient's bone.

10. The oral implant as claimed in claim 8 wherein
    said groove means comprising a longitudinal channel within said body portion extending downwardly from a position immediately beneath and adjacent said top portion; and
    said indented extending radially inwardly so as to be in communication with said longitudinal channel and be able to direct bone fragments into said longitudinal channel upon rotatable insertion of the implant in the patient's home.

11. The oral implant as claimed in claims 2 wherein
    said body portion having groove means to receive bone and allow bone to grow therein; and
    said cutting flutes extending radially inwardly from the periphery of said top portion so as to permit the outwardly-extending cutting surface of said cutting flutes to direct bone fragments into said groove means.

12. The oral implant as claimed in claim 11 wherein
    said groove means comprising a substantially circumferential groove immediately beneath but adjacent said top portion of said implant, extending radially inwardly to a distance less than diameter Dx; and
    said outwardly-extending cutting surface extending radially inwardly so as to be in communication with said circumferential groove and be able to direct bone fragments into said circumferential groove upon rotatable insertion of the implant in the patient's bone.

13. The oral implant as claimed in claim 11 wherein said groove means comprising a longitudinal channel within said body portion extending downwardly from a position immediately beneath and adjacent said top portion; and said outwardly-extending cutting surface extending radially inwardly so as to be in communication with said longitudinal channel and be able to direct bone fragments into said longitudinal channel upon rotatable insertion of the implant in the patient's bone.

* * * * *